(12) United States Patent
Chamney et al.

(10) Patent No.: US 11,079,397 B2
(45) Date of Patent: Aug. 3, 2021

(54) METHOD AND APPARATUS FOR DETERMINING A PATIENT'S FILTRATION RATE

(71) Applicant: FRESENIUS MEDICAL CARE DEUTSCHLAND GMBH, Bad Homburg (DE)

(72) Inventors: Paul Chamney, Tring (GB); Peter Wabel, Darmstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 67 days.

(21) Appl. No.: 15/558,224

(22) PCT Filed: Mar. 24, 2016

(86) PCT No.: PCT/EP2016/056545
§ 371 (c)(1),
(2) Date: Sep. 14, 2017

(87) PCT Pub. No.: WO2016/151087
PCT Pub. Date: Sep. 29, 2016

(65) Prior Publication Data
US 2018/0080947 A1    Mar. 22, 2018

(30) Foreign Application Priority Data
Mar. 24, 2015 (EP) .................................... 15160600

(51) Int. Cl.
| | | |
|---|---|---|
| G01N 33/50 | (2006.01) | |
| G01N 33/70 | (2006.01) | |
| A61B 5/0531 | (2021.01) | |
| A61B 5/0537 | (2021.01) | |

(52) U.S. Cl.
CPC ........... *G01N 33/70* (2013.01); *A61B 5/0531* (2013.01); *A61B 5/0537* (2013.01); *G01N 2800/347* (2013.01); *G01N 2800/52* (2013.01)

(58) Field of Classification Search
CPC ...... G01N 33/70; A61B 5/0531; A61B 5/0537
See application file for complete search history.

(56) References Cited

U.S. PATENT DOCUMENTS

2009/0054741 A1    2/2009    McAleer

FOREIGN PATENT DOCUMENTS

| JP | 2010-509018 | 3/2010 |
|---|---|---|
| WO | WO 2006/002656 | 1/2006 |

OTHER PUBLICATIONS

Kyle, Ursula et al. "Bioelectrical impedance analysis—part I: review of principles and methods." Clinical Nutrition (2004) 23 1226-1243. (Year: 2004).*
Milutinovic, Jovan et al. "Measurement of residual glomerular filtration rate in the patient receiving repetitive hemodialysis." Kidney International (1975) 8 185-190. (Year: 1975).*
Robert, Sylvie et al. "Predictability of creatinine clearance estimates in critically ill patients." Critical Care Medicine (1993) 21 1487-1495. (Year: 1993).*
Saxena, Sanjiv. "Timing of initiating dialysis." JIMSA (2012) 25 115. (Year: 2012).*
Shah, S. U. et al. "Use of diuretics in cardiovascular disease: (2) hypertension." Postgraduate Medical Journal (2004) 80 271-276. (Year: 2004).*
Baxmann et al. Influence of Muscle Mass and Physical Activity on Serum and Urinary Creatinine and Serum Cystatin C, Clinical Journal of the American Society of Nephrology, vol. 3, No. 2, pp. 348-354, Feb. 20, 2008.
Flury et al. Quantification of excretory renal function and urinary protein excretion by determination of body cell mass using bioimpedance analysis. BMC Nephrology, vol. 16, No. 1, Oct. 27, 2015, 174.
Rodrigo et al. Measurement of renal function in pre-ESRD patients. Kidney International, vol. 61, supplement 80 (2002), pp. S11-S17.
Cockcroft et al. Predicitin of Creatinine Clearance from Serum Creatinine. Nephron 16: 31-41 (1976).
Hallynck et al. Prediction of creatinine clearance from serum creatinine concentration based on lean body mass. Clinical Pharmacology and Therapeutics, 1981, vol. 30, No. 3, pp. 414-421.
Sylvie et al. Predictability of creatiine clearance estimates in critically ill patients. Critical Care Medicine, 1993, vol. 21, No. 10, pp. 1487-1495.
Saxena et al. Timing of Initiating Dialysis. Journal International/Medical Sciences Academy, 2012, vol. 25, No. 2, pp. 115-116.

* cited by examiner

*Primary Examiner* — Christopher Adam Hixson
(74) *Attorney, Agent, or Firm* — Jacobson Holman PLLC

(57) ABSTRACT

A method and an apparatus for determining or approximating a patient's glomerular filtration rate or a patient's creatinine clearance are disclosed. The method comprises the following steps: determining a serum creatinine concentration of the patient, determining a lean tissue mass of the patient, and determining the glomerular filtration rate of the patient or the creatinine clearance of the patient based on the serum creatinine concentration of the patient and the lean tissue mass of the patient.

18 Claims, 13 Drawing Sheets

METHOD AND APPARATUS FOR DETERMINING A PATIENT'S FILTRATION RATE

TECHNICAL FIELD

The present disclosure relates to a method for determining a patient's filtration rate, in particular a patient's glomerular filtration rate or an equivalent creatinine clearance. It relates further to a corresponding apparatus and to a diuretic. Finally, the present disclosure relates to a computer program product and a computer program.

BACKGROUND

Measurement of the GFR (glomerular filtration rate) is a commonly applied method to assess renal function in routine clinical practice. The management of patients with chronic kidney disease or declined renal function is to a large extent determined by the GFR and consequently stages of chronic kidney disease (CKD stages) 1-5 have been defined based on GFR. GFR (glomerular filtration rate) is an important clinical parameter used for the assessment of renal function. The majority of so called bed-side methods, i.e. methods for determining GFR in clinical practice, are based on the measurement of creatinine from a blood sample, the so called serum creatinine.

Creatinine is freely excreted by the kidney—if creatinine concentrations are known in blood and urine and urine output can be measured over 24 hours, the GFR can be determined. To that end direct measurement of GFR is possible using techniques such as creatinine clearance, [Rodrigo E, et. al.: Measurement of renal function in pre-ESRD patients. Kidney International Supplements 2002: May; (80): 11-17.] Methods of determining GFR requiring urine samples require reliable urine data, which is often problematic for a variety of reasons and as a result much effort has been expended on methods that require only a blood (or plasma) sample of creatinine.

One such method for estimating the GFR that requires only a blood (or plasma) sample of creatinine as sample from the patient is described in: Cockcroft D W, Gault M H: Prediction of creatinine clearance from serum creatinine. Nephron 1976, 16(1):31-41.

One drawback of this method and other methods relying only on a blood (or plasma) sample of creatinine as sample from the patient is the dependency of the applied equations from population specific parameters such as age or gender. Thus creatinine values are interpreted in the light of the part of the population the patient belongs to. Accordingly the accuracy of the estimation of the glomerular filtration rate provided by said methods is limited to the accuracy of associating a patient to a specific part of the population.

Therefore it is the subject of the present invention to overcome the above mentioned drawbacks and provide an improved method for determining the glomerular filtration rate or creatinine clearance of a patient.

SUMMARY

This subject is addressed by the teaching according to independent claims. Advantageous embodiments are described in the dependent claims.

In one embodiment a method for determining or approximating a patient's glomerular filtration rate or a patient's creatinine clearance is provided. The method comprises the following steps: determining a serum creatinine concentration of the patient, determining a lean tissue mass of the patient, and determining the glomerular filtration rate of the patient or the creatinine clearance of the patient based on the serum creatinine concentration of the patient and the lean tissue mass of the patient.

In one embodiment of the method the step of determining the lean tissue mass includes measuring the lean tissue mass.

In one embodiment the step of measuring the lean tissue mass includes applying a bioimpedance measurement. This provides for a particular convenient method.

In one embodiment the step of determining the serum creatinine concentration includes measuring the serum creatinine concentration from a blood sample. This provides for a particular reliable method.

In one embodiment the filtration rate $Q_{gfr}$ is determined by applying the formula:

$$Q_{gfr} = \frac{\alpha_{ltm} \cdot M_{LT_m}}{\beta_{ts} \cdot [Cr]_s},$$

wherein $M_{Lt\_m}$ is the lean tissue mass of the patient, $[Cr]_s$ is the serum creatinine concentration and $\alpha_{ltm}$ and $\beta_{ts}$ are proportionality constants. In particular $\alpha_{ltm}$ is a proportionality constant linking the generation rate of creatinine $G_{Cr}$ and the lean tissue mass $M_{LT\_m}$ as follows: $G_{Cr} = \alpha_{ltm} M_{LT}$ and $\beta_{ts}$ is a proportionality constant linking the glomerular filtration rate $Q_{gfr}$ and the creatinine clearance $K_{Cr\_WB}$ as follows: $Q_{gfr} \beta_{ts} = K_{Cr\_WB}$. A typical value for the proportionality constant $\alpha_{ltm}$ is: $\alpha_{ltm} = 0.0184$ mg/min/kg_$M_{LT}$. A typical value for the dimensionless proportionality constant $\beta_{ts}$ is 1.15.

In a further embodiment the method includes a step of determining a criterion for applying a renal replacement therapy to the patient based on the determined glomerular filtration rate or creatinine clearance of the patient, the renal replacement therapy including a dialysis treatment, in particular a hemodialysis treatment or a peritoneal dialysis treatment. The criterion may be a criterion whether to commence dialysis treatment for the patient or not. The criterion may be a criterion whether to change the treatment modality applied for the patient from a first treatment modality to a second treatment modality, e.g. from peritoneal dialysis to haemodialysis or vice versa. The criterion may be a criterion for applying a certain dosage when applying a renal replacement therapy, e.g. an amount of fluid to be withdrawn from a patient or a target clearance associated with a haemodialysis session.

In one embodiment the patient is a patient undergoing a renal replacement therapy, the renal replacement therapy including a peritoneal dialysis or a haemodialysis. In this embodiment the step of determining the serum creatinine concentration includes determining a first serum creatinine concentration at a first time between treatment sessions of the renal replacement therapy and determining a second serum creatinine concentration at a second time between treatment sessions of the renal replacement therapy. The first time may be immediately after concluding the renal replacement therapy, in case of haemodialysis: post HD, the second time may be when preparing for the renal replacement therapy, in case of haemodialysis: pre HD. In this embodiment the step the step of determining the patient's GFR or creatinine clearance is based on the first and on the second creatinine concentration.

In one particular embodiment the method includes a step of determining, in particular measuring the weight gain of the patient between the first time and the second time and wherein the step of determining the patient's GFR or creatinine clearance is based on the weight gain of the patient.

In one embodiment the method includes a step of determining the total body water of the patient, in particular measuring total body water by applying a bioimpedance measurement of a patient and wherein the step of determining the patient's GFR or creatinine clearance is based on the total body water of the patient.

In one embodiment of the method the patient's GFR or creatinine clearance is determined at a plurality of times and wherein a timely average is determined of the patient's GFR or creatinine clearance and wherein one or more extreme values or outliers are disregarded from the determination of the timely average. To that end a median filter may be applied for filtering the time series. By that approach, influences on the measurement stemming from variations of the diet of the patient may be suppressed.

In one embodiment the method includes a step of determining a criterion for the subscription of a medication promoting the production of urine for use in the treatment of a patient suffering from a reduced glomerular filtration rate or creatinine clearance, i.e. a diuretic, based on the determined glomerular filtration rate or creatinine clearance of the patient. E.g. the criterion may be a criterion whether to commence a diuretics therapy for a patient or not. Alternatively or in addition the criterion may be a criterion for determining a dosage of a diuretic for a patient. In one embodiment a medication, preferably a diuretic to be administered to a patient is provided, wherein the dosage and/or the administration scheme of the medication is determined based on said determined criterion.

In a further embodiment an apparatus for determining or approximating a patient's GFR or a patient's creatinine clearance is provided. The apparatus comprises a first determination unit configured to determine a serum creatinine concentration of the patient, a second determination unit configured to determine a lean tissue mass of the patient, and a processing unit configured to determine the GFR of the patient or the creatinine clearance of the patient based on the serum creatinine concentration of the patient and the lean tissue mass of the patient.

The apparatus is susceptible to the same advantageous modifications or improvements as the above disclosed method.

In one embodiment a first and a second mode of operation are defined for the processing unit and wherein the processing unit is configured to perform the method of determining the filtration rate $Q_{gfr}$ by applying the formula:

$$Q_{gfr} = \frac{\alpha_{ltm} \cdot M_{LT_m}}{\beta_{ts} \cdot [Cr]_s},$$

as described above in the first mode of operation and wherein the processing unit is configured to perform the method of determining the serum creatinine concentration that includes determining a first serum creatinine concentration at a first time between treatment sessions of a renal replacement therapy and determining a second serum creatinine concentration at a second time between treatment sessions of the renal replacement therapy as has been described above in the second mode of operation. By this an apparatus for determining or approximating a patient's GFR or a patient's creatinine clearance is provided that can be applied for all stages of renal therapy including pre-ESRD therapy, renal replacement therapy and transplantation.

DETAILED DESCRIPTION OF THE DRAWINGS

Figure 1:
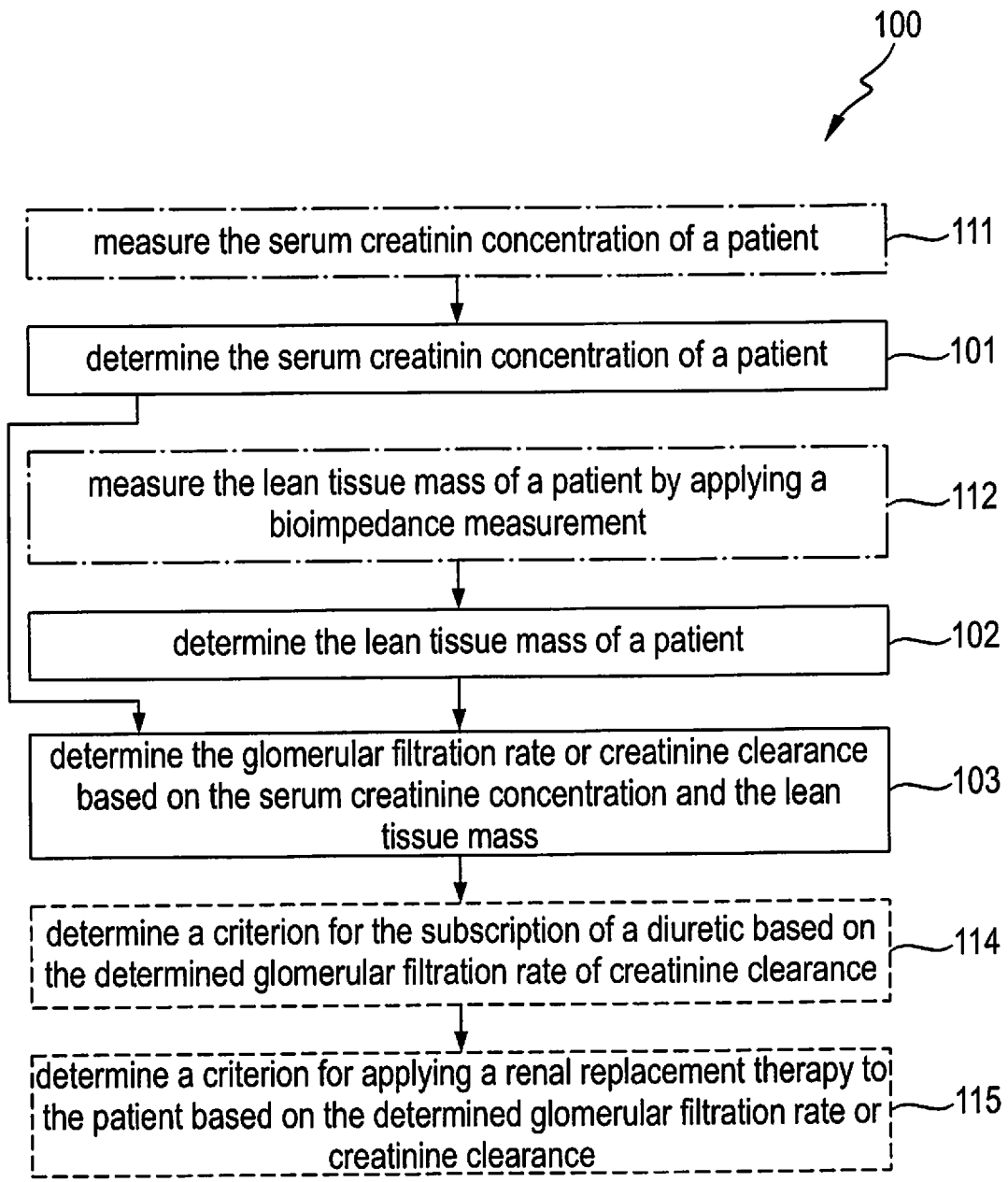
FIG. 1 depicts a flow diagram of a method for determining a filtration rate or clearance of a patient.

FIG. 1 depicts a method 100 for determining or approximating a patient's glomerular filtration rate (GFR) or a patient's creatinine clearance.

The method 100 includes a step 101 of determining a serum creatinine concentration of the patient, in one embodiment the step 101 is preceded with or includes a step 111 of measuring the serum creatinine concentration on a blood sample previously taken from the patient. Alternatively, the serum creatinine concentration is inputted manually into a user interface of the system 300.

The method 100 further includes a step 102 of determining a lean tissue mass of the patient. In one embodiment the step 102 is preceded with or includes a step 112 of measuring the lean tissue mass by applying a bioimpedance measurement.

The method 100 also includes a step 103 to determine the GFR of the patient or the creatinine clearance of the patient based on the serum creatinine concentration of the patient determined in step 101 and based on the lean tissue mass of the patient determined in step 102.

In one embodiment the creatinine clearance $K_{Cr\_WB}$ is determined in step 103 by applying the formula:

$$K_{Cr\_WB} = \frac{\alpha_{ltm} \cdot M_{LT\_m}}{[Cr]_s}$$

wherein $M_{LT\_m}$ is the lean tissue mass of the patient, $[Cr]_s$ is the serum creatinine concentration and $\alpha_{ltm}$ is a proportionality constant linking the generation rate of creatinine $G_{Cr}$ and the lean tissue mass $M_{LT\_m}$ as follows: $G_{Cr} = \alpha_{ltm} M_{LT}$. A typical value for the proportionality constant $\alpha_{ltm}$ is: $\alpha_{ltm} = 0.0184$ mg/min/kg_$M_{LT}$.

In another embodiment the glomerular filtration rate $Q_{gfr}$ is determined in step 103 as follows:

$$Q_{gfr} = \frac{\alpha_{ltm} \cdot M_{LT_m}}{\beta_{ts} \cdot [Cr]_s},$$

wherein $\alpha_{ltm}$, $[Cr]_s$, and $M_{LT\_m}$ are as introduced before and $\beta_{ts}$ is a proportionality constant linking the glomerular filtration rate $Q_{gfr}$ and the creatinine clearance $K_{Cr\_WB}$ as follows: $Q_{gfr}\beta_{ts}=K_{Cr\_WB}$.

A typical value for the dimensionless proportionality constant $\beta_{ts}$ is 1.15. The proportionality constant $\beta_{ts}$ accounts for the secretion of creatinine by the proximal tubes of the kidney.

In one embodiment the method 100 includes a step 114 of determining a criterion for the subscription of or a dosage or a dosing scheme for a medication promoting the production of urine for use in the treatment of a patient suffering from a reduced GFR or creatinine clearance, i.e. a diuretic, based on the determined GFR or creatinine clearance of the patient. E.g. the criterion may be a criterion whether to commence a diuretics therapy for a patient or not.

In a further embodiment the method 100 includes a step 115 of determining a criterion for applying a renal replacement therapy to the patient based on the determined GFR or creatinine clearance of the patient, the renal replacement therapy including a dialysis treatment, in particular a haemodialysis treatment or a peritoneal dialysis treatment. The criterion may be a criterion whether to commence dialysis treatment for the patient or not. The criterion may be a criterion whether to change the treatment modality applied for the patient from a first treatment modality to a second treatment modality, e.g. from peritoneal dialysis to haemodialysis or vice versa. The criterion may be a criterion for applying a certain dosage when applying a renal replacement therapy, e.g. an amount of fluid to be withdrawn from a patient or a target clearance associated with a haemodialysis dialysis session.

Figure 2:
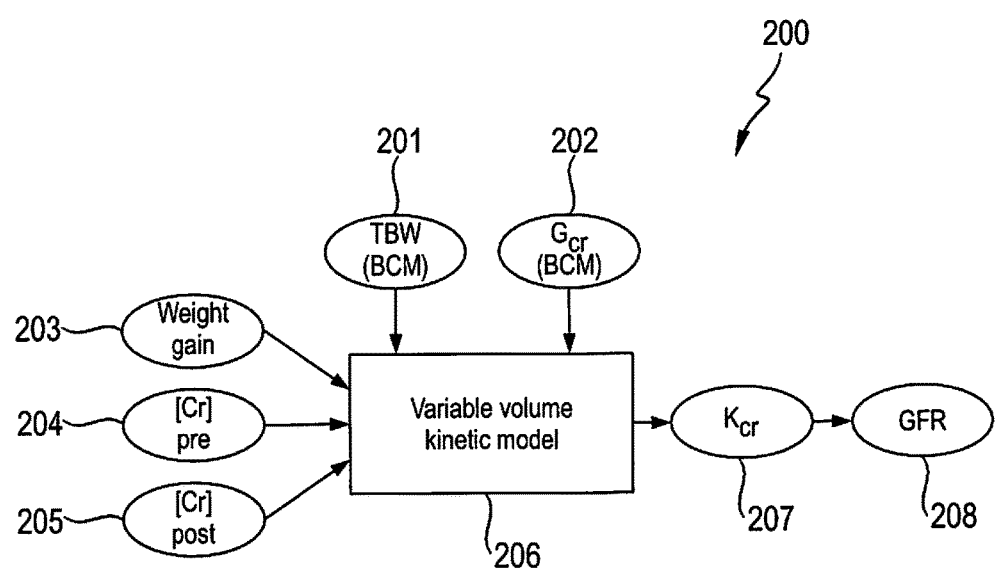
FIG. 2 depicts a further flow diagram for determining a filtration rate or a clearance of a patient.

FIG. 2 depicts a method 200 for determining the creatinine clearance and/or the GFR of a patient undergoing a renal replacement therapy, the renal replacement therapy including a peritoneal dialysis or a HD (haemodialysis) treatment. The method 200 includes a step 205 of determining a first serum creatinine concentration at a first time between treatment sessions of the renal replacement therapy, the first time preferably being immediately after concluding the renal replacement therapy, in case of haemodialysis: post HD. In the following the serum creatinine concentration at the first time shall be referred to as: $C_0=[Cr]_s$ (Post).

The method 200 further includes a step 204 of determining a second serum creatinine concentration at a second time between treatment sessions of the renal replacement therapy, in case of haemodialysis: pre HD. The serum creatinine concentration at the second time shall be referred to as: $C=[Cr]_s$ (Pre).

The method 200 further includes a step 203 of determining, in particular measuring the weight gain of the patient between the first time and the second time. The weight gain will be referred to as: Q·t, wherein t is the time that has elapsed between the first time and the second time, in a preferred embodiment t is the time that has elapsed between treatment sessions.

The method 200 further includes a step 201 of determining the total body water of the patient, in particular measuring a total body water by applying a bioimpedance measurement of a patient, preferably at the first time, more preferably immediately after conducting renal replacement therapy, i.e. post HD. The TBW (total body water) shall be referred to as $V_0$=TBW (Post).

Furthermore, the method 200 includes a step 202 of determining creatinine generation rate from the lean tissue mass of the patient which has been previously determined by applying a bioimpedance measurement.

Thus, the creatinine generation rate may be expressed as $G_{Cr}=\alpha_{ltm}M_{LT}$, wherein the lean tissue mass $M_{LT\_m}$ is the lean tissue mass of the patient and $\alpha_{ltm}$ is a proportionality constant linking the generation rate of creatinine and the lean tissue mass $M_{LT\_m}$ as has been described above in relation to FIG. 1.

Finally, the method 200 includes a step 206 of determining the creatinine clearance $K_{cr}$ based on the serum creatinine concentration $C_o$ at the first time, i.e. preferably after renal replacement therapy, the serum creatinine concentration C at the second time, i.e. preferably before renal replacement therapy, the creatinine generation rate $G=G_{Cr}$, the total body water $V_0$ and the weight gain Q·t between the first time and the second time, i.e. preferably between treatment sessions.

To that end the following formula relating the creatinine clearance $K=K_{cr}$ to the input parameters G, C, $C_0$, $V_0$ and Q·t may be applied:

$$C = \frac{G}{K+Q} \cdot \left(1 - \left(\frac{[V_0+Q\cdot t]}{V_0}\right)^{\frac{1}{\alpha}}\right) + C_0 \cdot \left(\frac{[V_0+Q\cdot t]}{V_0}\right)^{\frac{1}{\alpha}}$$

$$\text{wherein } \alpha = \frac{-Q}{K+Q}$$

and wherein the formula is solved, preferably iteratively, for K.

The value of the creatinine clearance K is determined at a step 207 and a glomerular filtration rate GFR=$Q_{GFR}$ is determined using $K_{Cr\_WB}$=K and $$Q_{gfr} = \frac{K_{Cr\_WB}}{\beta_{ts}}$$

in step 208, wherein $\beta_{ts}$ is as explained above in relation to FIG. 1.

The glomerular filtration rate $Q_{gfr}$ or creatinine clearance $K_{Cr\_WB}$ thus determined may be utilized as a criterion for applying certain dose of a renal replacement therapy as has been described above in relation to FIG. 1.

Figure 3:
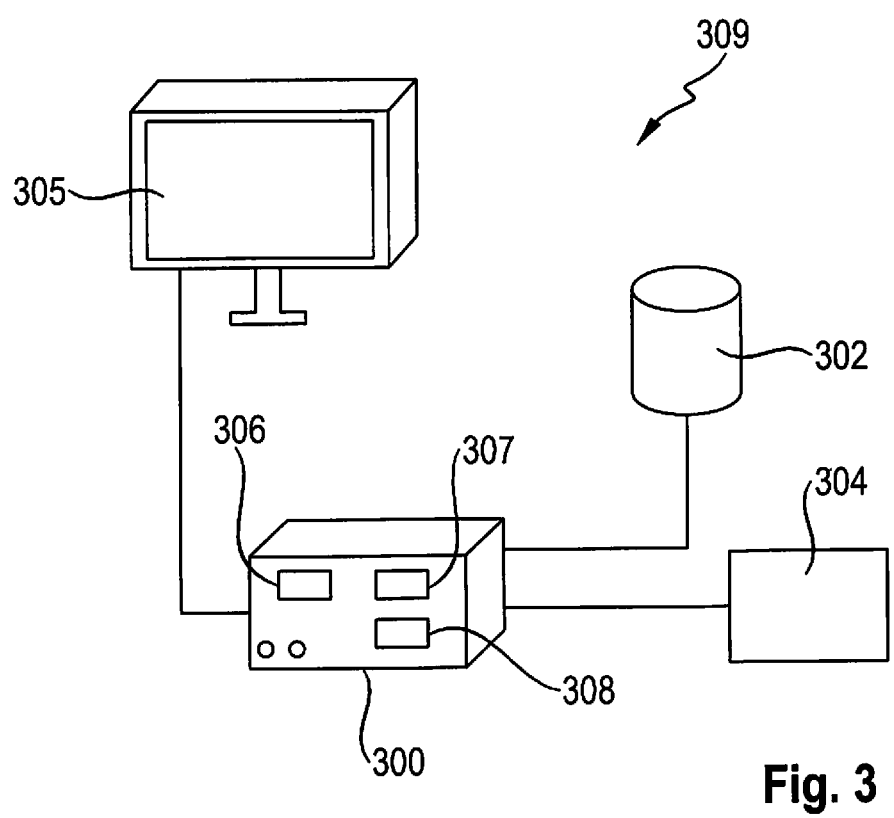
FIG. 3 shows a first apparatus according to the present disclosure comprising a controller for carrying out a method in accordance with the present teaching.

FIG. 3 depicts a system 309 adapted for carrying out any of the methods described above in relation to FIG. 1 or FIG. 2. The system 309 comprises an apparatus 300.

The apparatus 300 is connected to an external database 302 comprising the results of the measurements carried out on a patient and all other data needed for one of the described methods. The database 302 may also be an internal means to the apparatus 300.

The apparatus 300 may optionally have means 304 for inputting data and providing the data to the processing unit 306. Such data may be any data required in connection with a method described in relation to FIG. 1 or FIG. 2.

The apparatus 300 comprises a first determination unit 307 configured to determine a serum creatinine concentration of the patient, either based on a measurement or on data received from the database 302 or from the means 304.

Furthermore the apparatus 300 comprises a second determination unit 308 configured to determine a lean tissue mass of the patient, either based on a measurement or on data received from the database 302 or from the means 304.

Still further the apparatus 300 comprises the processing unit 306 configured to determine the GFR of the patient or the creatinine clearance of the patient based on the serum creatinine concentration of the patient and the lean tissue mass of the patient.

The processing unit may be further adapted to carry out any of the methods described above in relation to the description of FIG. 1 and FIG. 2.

The results of the determination can be displayed on the monitor 305 or stored by means of the database 302 or any other storage means.

Figure 4:
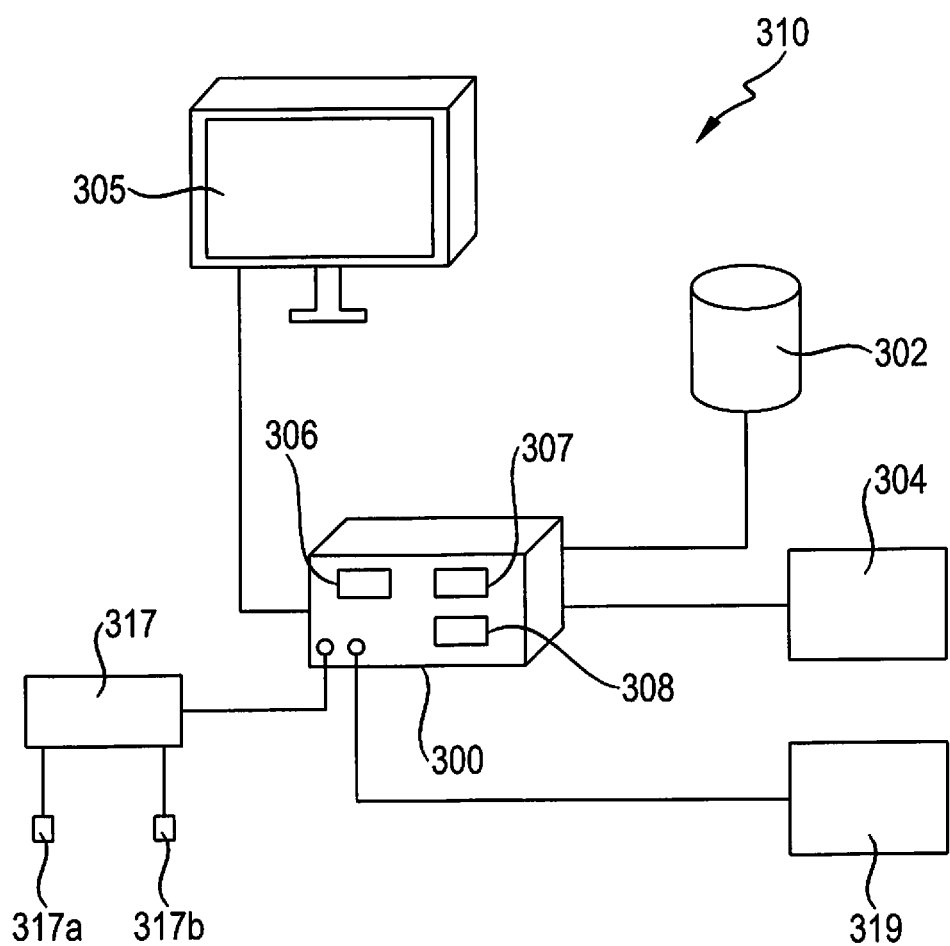
FIG. 4 shows a second apparatus according to the present disclosure comprising a controller for carrying out a method in accordance with the present teaching.

FIG. 4 depicts a system 310 which is a modification of the system 309. As can be seen from the system 310 depicted in FIG. 4, the apparatus 300 may be connected (by means of a wire or wireless) with a bioimpedance measurement means 317 as one measurement means for providing measurement results for determining the lean tissue mass of the patient to the determining unit 308. Alternatively or in addition the bioimpedance measurement means 317 may provide measurement results to determine the total body water of the patient to the processing unit 306.

Determining the lean tissue mass of the patient from bioimpedance measurements and/or to determining the total body water of the patient from bioimpedance measurements may be performed as described in WO 2006/002685 A1, the disclosure of which is hereby explicitly incorporated in the present application by reference.

Generally the bioimpedance measurement means 317 may be provided in addition to the database 302 comprising the results of the measurement and the data required for the methods described above in relation to FIG. 1 or FIG. 2 or in place of the database 302.

The bioimpedance measurement means 317 can be capable of automatically compensating for influences on the impedance data like contact resistances.

An example of a bioimpedance measurement means 317 is a device from Xitron Technologies, distributed under the trademark Hydra™ that is further described in WO 92/19153, the disclosure of which is hereby explicitly incorporated in the present application by reference.

The bioimpedance measurement means 317 may comprise various electrodes for being attached to the patient. In FIG. 4 only two electrodes 317a and 317b are shown which are attached to the bioimpedance measurement means 317. Additional electrodes are of course also contemplated.

Each electrode implied can comprise two or more ("sub"-) electrodes in turn. Electrodes can comprise a current injection ("sub"-) electrode and a voltage measurement ("sub"-) electrode. That is, the electrodes 317a and 317b shown in FIG. 4 can comprise two injection electrodes and an two voltage measurement electrodes (i.e. four electrodes in total).

The apparatus may have further means 319 for measuring body parameters of the patient required for a method to be carried out by the apparatus. The means 319 for measuring a body parameter may be a scale for measuring the patient's weight or any laboratory equipment required for determining the patient's serum creatinine concentration.

Figure 5:
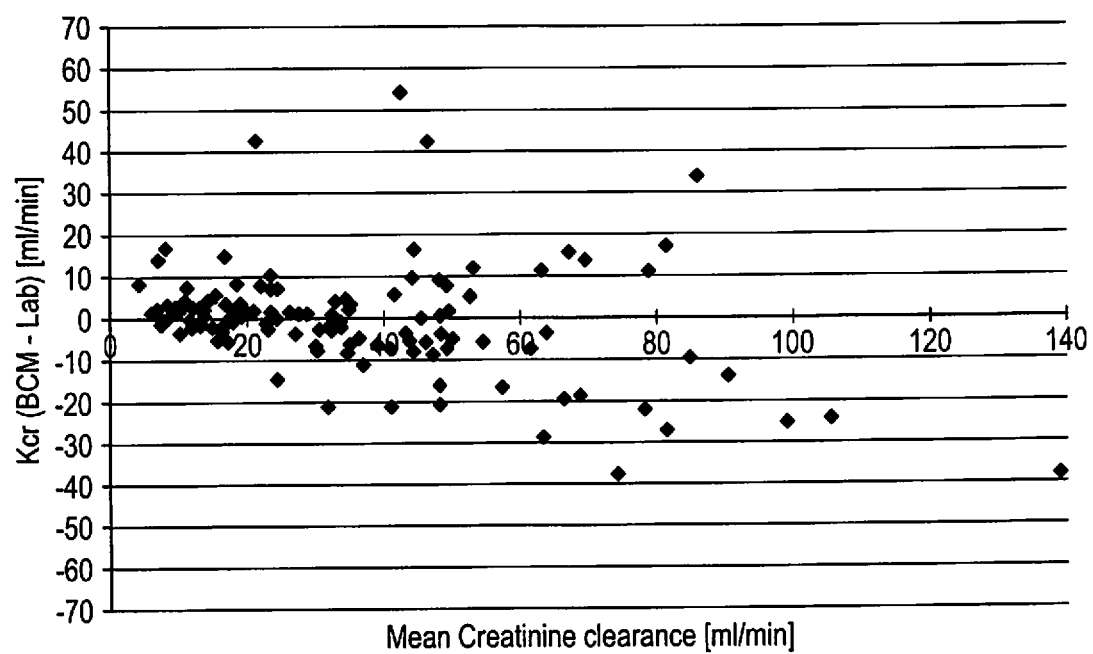
FIG. 5-7 respectively show a scatter diagram of a statistical analysis of comparing methods of determining creatinine clearance.

FIG. 5 depicts a statistical analysis comparing results of a creatinine clearance determined using the method described in relation to FIG. 1 and a method from the related art which is based on using both blood and urine samples. Both methods were applied to a patient cohort including 124 patients not undergoing renal replacement therapy, so called pre-ESRD (pre-end-stage renal disease) patients. The measurements from the related art serve as a reference and are denoted as 'Lab'. FIG. 5 is a plot of a statistical analysis plotting differences between the measurement results from the different methods against the mean value from both methods. The difference between measurement values is plotted on the vertical axis, wherein the mean value is plotted on the horizontal axis. The result from the method described in relation to FIG. 1 is denoted as 'BCM', whereas the result from the method of the related art is denoted as 'Lab'. Comparing the result of the letter method and the method from the prior art applying Bland-Altman analysis, this leads to a mean difference of −0.89±13.2 ml/min.

Figure 6:
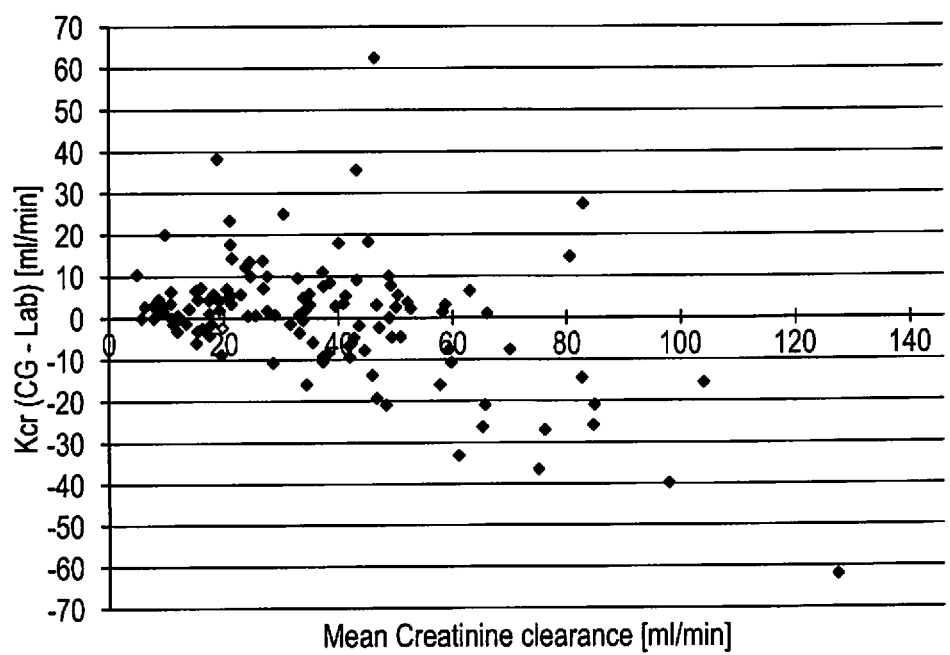

FIG. 6 depicts a similar statistical analysis as the statistical analysis provided in FIG. 5, wherein the results of a further method from the related art, the so called Cockroft Gault method are compared with results of the method which is based on blood and urine samples on the same above mentioned patient cohort, wherein results of the Cockroft Gault method are noted as 'CG'. The result of the Bland-Altman analysis provides for an agreement of 0.3±14.7 ml/min.

Figure 7:
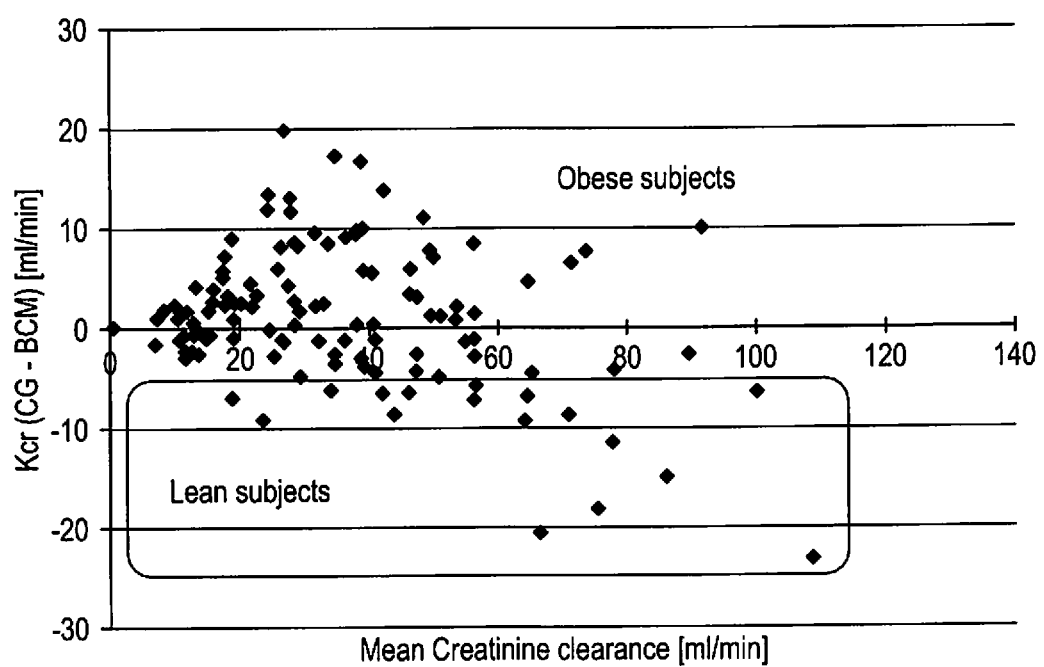

FIG. 7 depicts a similar statistical analysis as the statistical analysis provided in FIGS. 5 and 6, wherein the results of the method described in relation to FIG. 1 are compared to results from the Cockroft Gault method. As can be seen differences between the two methods may be attributed to whether the patient may be diagnosed 'obese' or 'lean'.

FIGS. 8-13 depict simulation results of a patient body model having a varying body composition and a constant glomerular filtration rate.

Figure 8:
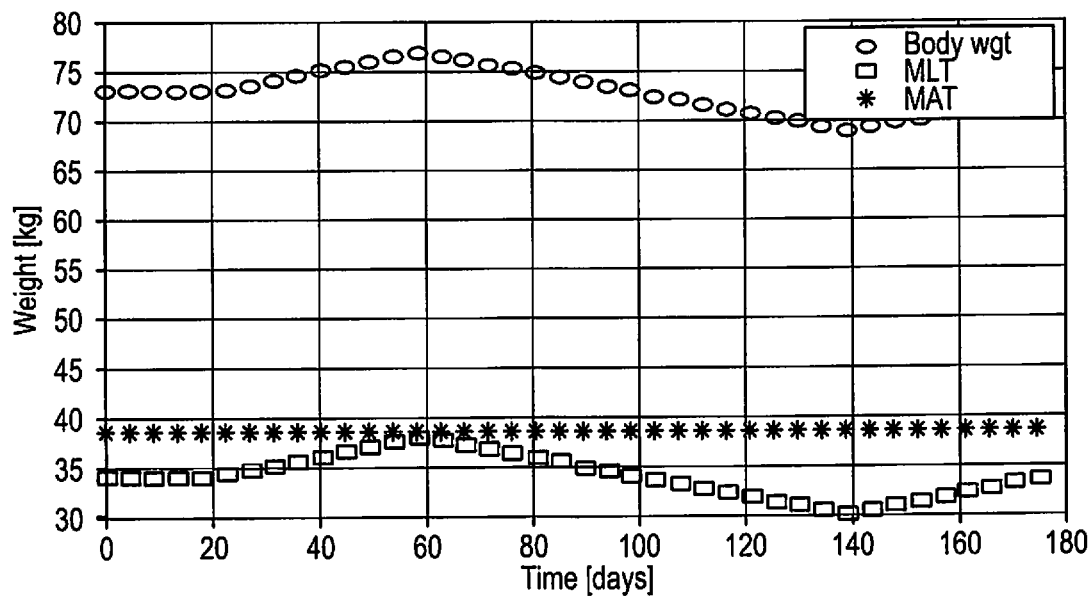
FIG. 8-13 respectively show simulated measurement results comparing a method in accordance with the present teaching and conventional methods of determining GFR.
Figure 8:
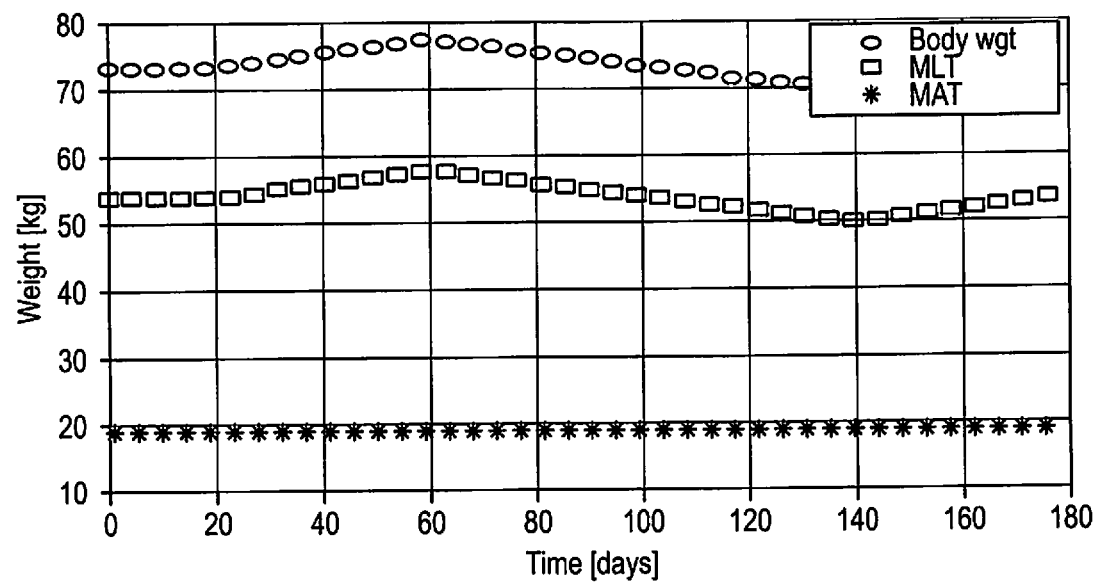
Figure 10:
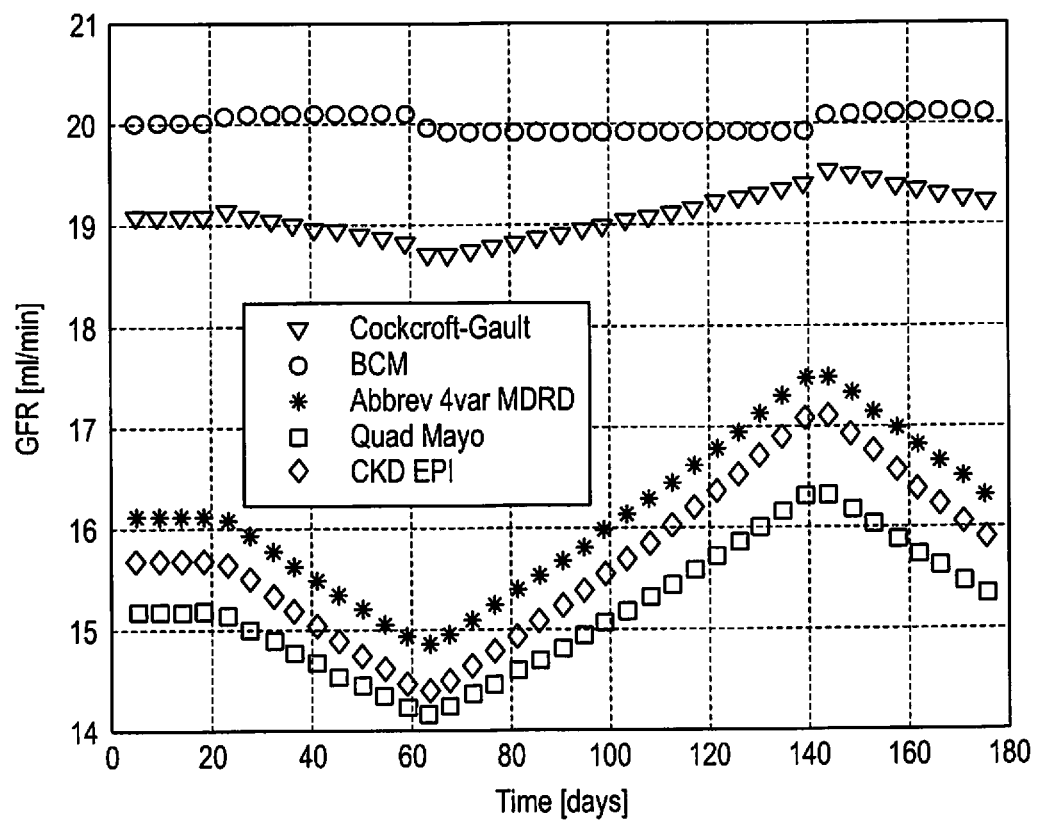
Figure 11:
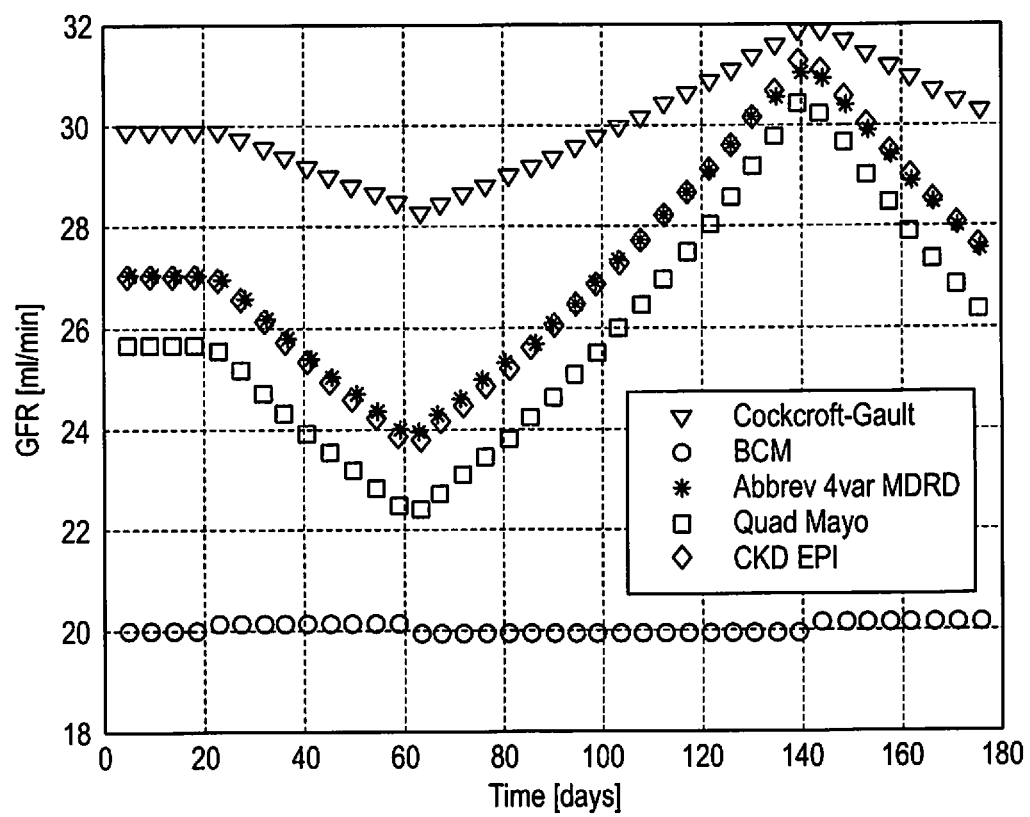
Figure 12:
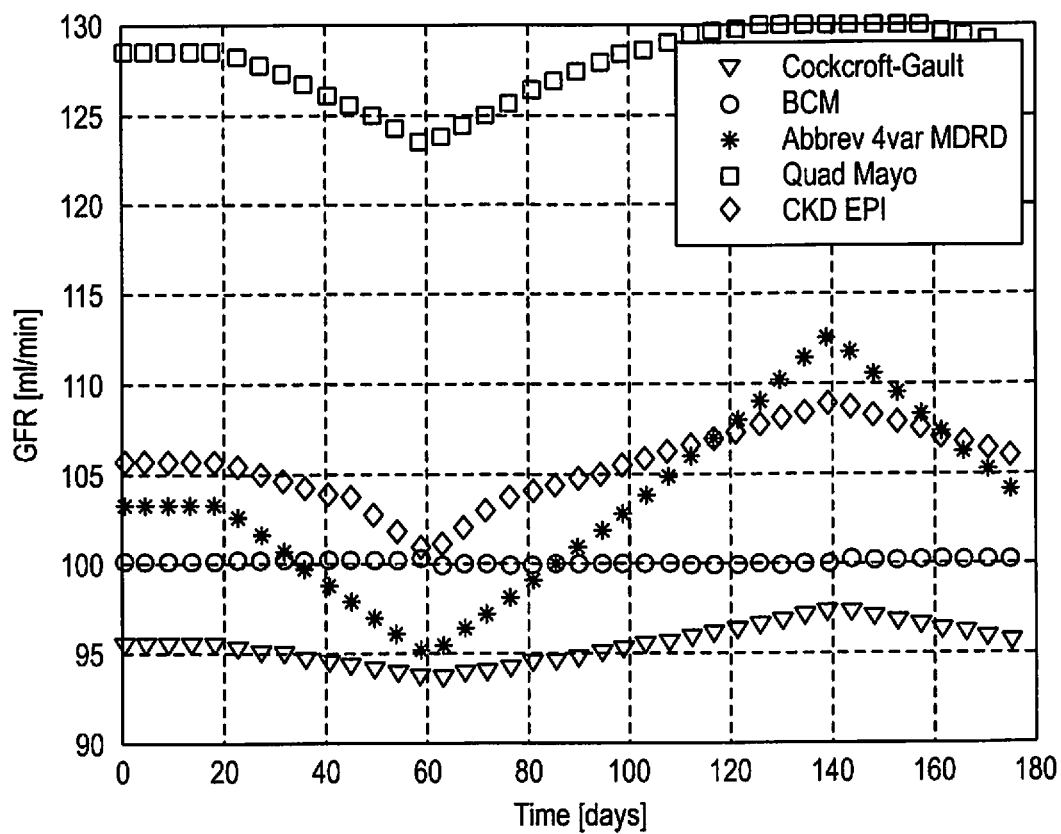

In particular, FIG. 8 depicts two subjects having different body compositions namely an obese (upper diagram) and lean subject (lower diagram), that are used for the simulation, the result of which are depicted in FIGS. 10-13. In particular the lower of the diagrams in FIG. 8 represents the body composition that has been fed into the simulations, the result of which are shown in FIG. 10 and FIG. 12. The upper diagram of FIG. 8 represents the body composition used in the simulations depicted in FIG. 11 and in FIG. 13.

Both in the upper and the lower diagram of FIG. 8, values of the total body weight at different simulated days are depicted with elliptical dots. The total body weight is composed of MAT (mass of adipose tissue or adipose tissue mass) and MLT (mass of lean tissue or lean tissue mass). Cross like dots represent the evolution of the adipose tissue mass which is substantially constant, rectangular dots represent the varying lean tissue mass.

Figure 9:
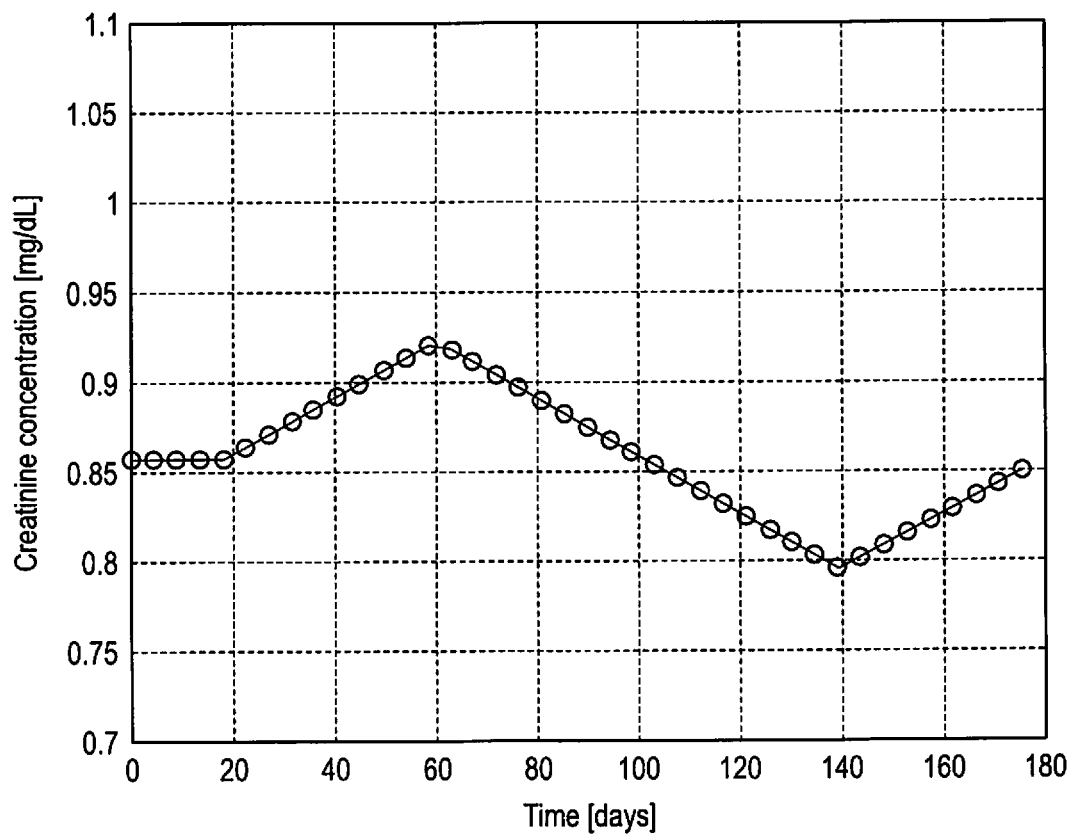

FIG. 9 depicts the result of a simulation, simulating the timely evolution of the creatinine concentration in the model body depicted in the lower diagram of FIG. 8.

The simulation of the timely evolution of the creatinine concentration is based on the following assumptions:

The rate of change of creatinine mass with time $$\frac{dM_{Cr}}{dt}$$

depends on the generation rate of creatinine $G_{Cr}$, creatinine concentration [Cr] creatinine clearance $K_{Cr}$ and also the rate of change of total body water $$\frac{dV_{TBW}}{dt}.$$

Thus, $$\frac{dM_{Cr}}{dt} = [Cr]\frac{dV_{TBW}}{dt} + V_{TBW}\frac{d[CR]}{dt} = G_{Cr} - K_{Cr}[Cr]$$

Rearranging for d[Cr]/dt leads to:

$$\frac{d[Cr]}{dt} = \frac{G_{Cr} - K_{Cr}[Cr] - [Cr]\frac{dV_{TBW}}{dt}}{V_{TBW}}$$

This equation may be integrated to simulate a timely evolution of the creatinine concentration depending on the creatinine clearance $K_{Cr}$ and the body composition parameters fed into the simulation. The creatinine clearance, $K_{Cr}$ is related to the glomerular filtration rate $Q_{gfr}$ from the relationship $Q_{gfr}\beta_{ts}=K_{Cr\_WB}$ The distribution space of creatinine in the body is considered equivalent to the total body water ($V_{TBW}$) and hence this may be determined from the methods described in described in WO 2006/002685, i.e.

$$V_{TBW}=H_{tw\_LT}M_{LT}+H_{tw\_AT}M_{AT}+M_{FO}$$

Where
$M_{AT}$ is the adipose tissue mass
$M_{LT}$ is the lean tissue mass
$Ht_{w\_LT}$ and $H_{tw\_AT}$ are the hydration coefficients of lean and adipose tissue
$M_{FO}$ is the mass of fluid overload (OH (overhydration) where present.

Over time (weeks to months) changes in body composition will modify the total body, changing the creatinine distribution space. Therefore, differentiating equation for $V_{TBV}$ leads to:

$$\frac{dV_{TBW}}{dt} = H_{tw\_LT}\frac{dM_{LT}}{dt} + H_{tw\_AT}\frac{dM_{AT}}{dt} + \frac{dM_{FO}}{dt}$$

The time dependent creatinine concentration is subsequently fed into the method for determining the GFR described in relation to the method of FIG. 1. In addition, the glomerular filtration rate GFR is determined from the time dependent creatinine concentration and other parameters according to further methods for determining an estimate of the GFR from the prior art, that will be termed conventional methods in the following.

The following conventional methods were used to simulate estimates of the GFR and the results from the simulated estimates are depicted in FIGS. 10-13.

The results from the method described in: "Cockcroft D W, Gault M H: Prediction of creatinine clearance from serum creatinine. Nephron 1976, 16(1):31-41", are termed "Cockroft-Gault" and are plotted as triangles.

The results from applying the method described in relation to FIG. 1 are termed "BCM" and are plotted as circles.

The results from the method described in: "A. S. Levi T G, J. W. Kusek, G. J. Beck: A simplified equation to predict glomerular filtration rate from serum creatinine [abstract] J Am Soc Nephrol 2000, 11:155A" are termed "Abbrev 4 var MDRD" (short for Abbreviated 4 variable Modification of Diet in Renal Disease) and are plotted as stars.

The results from the method described in: "Rule A D, Larson T S, Bergstralh E J, Slezak J M, Jacobsen S J, Cosio F G: Using serum creatinine to estimate glomerular filtration rate: accuracy in good health and in chronic kidney disease. Annals of internal medicine 2004, 141(12):929-937." are termed "Quad Mayo" (short for: Quadratic Mayo Clinic) and are plotted as squares.

The results from the method described in: Murata K, Baumann N A, Saenger A K, Larson T S, Rule A D, Lieske J C: Relative performance of the MDRD and CKD-EPI equations for estimating glomerular filtration rate among patients with varied clinical presentations. Clinical journal of the American Society of Nephrology: CJASN 2011, 6(8):1963-1972, are termed "CKD EPI" and are plotted as rhombs.

FIG. 10 depicts the simulated measurement results for a body model simulating a lean patient having a glomerular filtration rate $Q_{gfr}$=20 ml/min and a relative fat mass of 20%.

If the lean tissue mass is varied in accordance with FIG. 8, then the results of FIG. 10 shows than in lean subjects at low glomerular filtration rates the conventional methods for determining the glomerular filtration rate underestimate the reference GFR that has been fed into the simulation. Remarkably the conventional methods show an apparent variation in the simulated measurement of the GFR due to the change in creatinine concentration. The reason for this is that the conventional methods for determining the GFR do not compensate for the variations of the lean tissue.

FIG. 11 depicts the simulated measurement results for a body model simulating a patient having a glomerular filtration rate $Q_{gfr}$=20 ml/min and a fraction of 40% adipose tissue, i.e. a model of a patient that that may be characterized an obese subject. As the simulation results show, in the scenario of an obese subject the conventional methods for estimating GFR overestimate the GFR that has been inputted into the simulation.

FIG. 12 depicts the simulated measurement results for a body model simulating a patient having a glomerular filtration rate $Q_{gfr}$=100 ml/min and a fraction of 20% adipose tissue, i.e. fat, i.e. simulating a patient that that may be characterized an lean subject at a physiological GFR. At this level of the GFR and in lean subjects the agreement between the GFR that has been inputted into the simulation which depicted with BCM and most of the results from the conventional methods is good (typically ca. ±5 ml/min). The method termed "Quadratic Mayo Clinic" significantly overestimates the inputted GFR.

Figure 13:
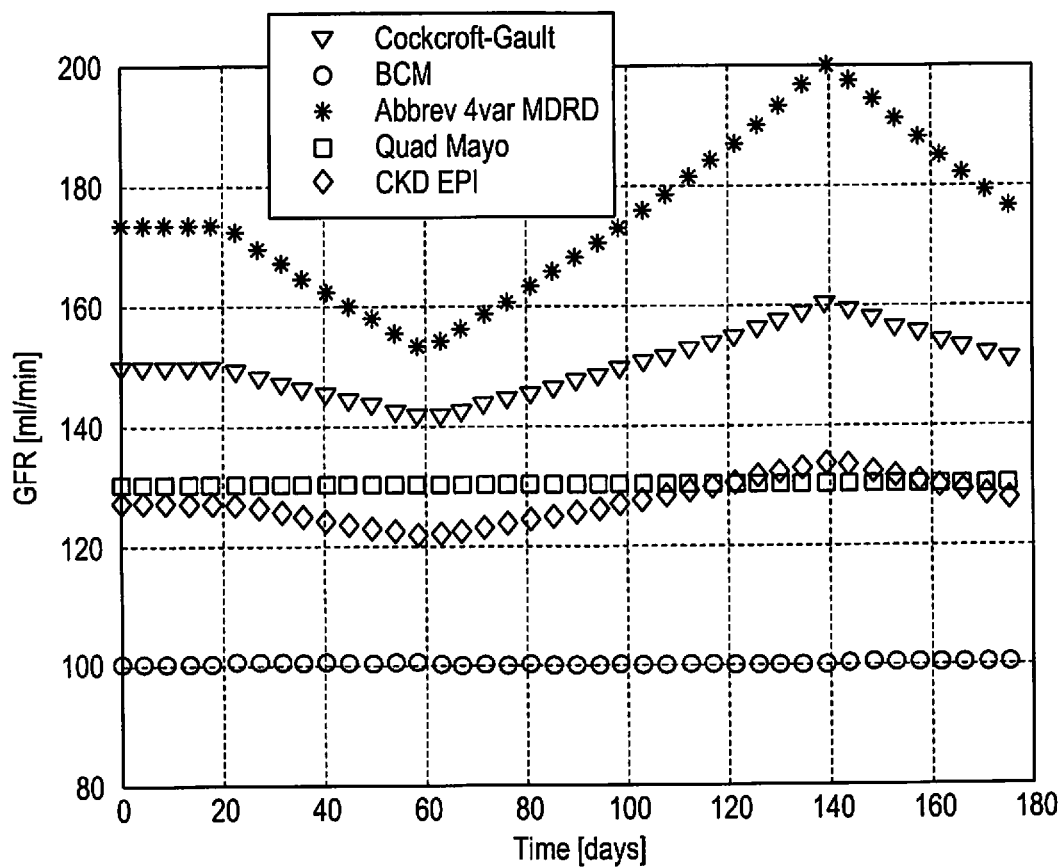

FIG. 13 depicts the simulated measurement results for a body model simulating a patient having a glomerular filtration rate $Q_{gfr}$=100 ml/min and a fraction of 40% adipose tissue, i.e. fat, i.e. simulating a patient that that may be characterized an obese subject at a physiological glomerular filtration rate. As the simulation results show, a physiological GFR in an obese subject represents some of the largest sources of error in conventional methods of determining the GFR. Most of the conventional methods generate GFR levels above the upper physiological range of GFR.

FIGS. 10-13 depict the magnitude of errors incurred using conventional methods for estimating GFR that are used in routine practice in comparison with simulation results from applying the method described in relation to FIG. 1. The simulations show that assuming there is no change in kidney function the and thus GFR as an input into the simulation, the simulated measurement result from applying the method of FIG. 1 also remains unchanged independent of variations in muscle mass (MLT). The concentration of creatinine and its rate of generation will vary in response to MLT changes, but this should not affect the GFR. In other words, the GFR should be independent of variations in body composition. This is in contrast to the conventional methods for estimating GFR, showing a variation of the GFR estimate, depending on the variation of the body composition inputted into the simulation.

The invention claimed is:

1. Method for determining or approximating a patient's glomerular filtration rate or a patient's creatinine clearance in a patient undergoing intermittently a renal replacement treatment, the method comprising the steps of:
   determining a serum creatinine concentration of the patient,
   determining a lean tissue mass of the patient,
   determining the glomerular filtration rate of the patient or the creatinine clearance of the patient without using age or gender of the patient and based on the serum creatinine concentration of the patient and the lean tissue mass of the patient,
   determining which of chronic kidney disease (CKD) stages 1-5 the patient is in based on the determined glomerular filtration rate or creatinine clearance, and
   determining a criterion for applying a renal replacement therapy to the patient based on the determined glomerular filtration rate or creatinine clearance of the patient,
   wherein the step of determining the serum creatinine concentration includes determining a first serum creatinine concentration at a first time between treatment sessions and determining a second serum creatinine concentration at a second time between treatment sessions and wherein the step of determining the patient's glomerular filtration rate or creatinine clearance is based on the first creatinine concentration and on the second creatinine concentration.

2. Method according to claim 1, wherein the step of determining the lean tissue mass includes measuring the lean tissue mass.

3. Method according to claim 2, wherein the step of measuring the lean tissue mass includes applying a bioimpedance measurement.

4. Method according to claim 1, wherein the step of determining the serum creatinine concentration includes measuring the serum creatinine concentration from a blood sample of the patient.

5. Method according to claim 1, wherein the glomerular filtration rate $Q_{gfr}$ is determined by applying the formula:

$$Q_{gfr} = \frac{\alpha_{ltm} \cdot M_{LT_m}}{\beta_{ts} \cdot [Cr]_s},$$

wherein $M_{LTm}$ is the lean tissue mass of the patient, $[Cr]_s$ is the serum creatinine concentration and $\alpha_{ltm}$ and $\beta_{ts}$ are proportionality constants.

6. Method according to claim 1, further comprising the step of measuring the weight gain of the patient between the first time and the second time and wherein the step of determining the patient's glomerular filtration rate or creatinine clearance is based on the weight gain of the patient.

7. Method according to claim 1, further comprising the step of measuring a total body water of the patient by applying a bioimpedance measurement and wherein the step of determining the patient's glomerular filtration rate or creatinine clearance is based on the total body water of the patient.

8. Method according to claim 1, wherein the patient's glomerular filtration rate or creatinine clearance is determined at a plurality of times and wherein a timely average is determined of the patient's glomerular filtration rate or creatinine clearance and wherein an outlier is disregarded from the determination of the timely average.

9. Method according to claim 1, further comprising the step of determining a criterion for the prescription of a diuretic based on the determined glomerular filtration rate or creatinine clearance of the patient.

10. Apparatus for determining or approximating a patient's glomerular filtration rate or a patient's creatinine clearance, the apparatus comprising:
    a first receiver configured to receive a serum creatinine concentration of the patient, a second receiver configured to include or connect to a measuring unit for measuring a lean tissue mass of the patient, and a central processing unit configured to determine (i) the glomerular filtration rate $Q_{gfr}$ of the patient by applying the formula $$Q_{gfr} = \frac{\alpha_{ltm} \cdot M_{LT_m}}{\beta_{ts} \cdot [Cr]_s}$$

wherein $M_{LTm}$ is the lean tissue mass of the patient, $[Cr]_s$ is the serum creatinine concentration, and $\alpha_{ltm}$ and $\beta_{ts}$ are proportionality constants, or (ii) the creatinine clearance of the patient by applying the formula $$K_{Cr\_WB} = \frac{\alpha_{ltm} \cdot M_{LT\_m}}{[Cr]_s}$$

wherein $M_{LT\_m}$ is the lean tissue mass of the patient, $[Cr]_s$ is the serum creatinine concentration and $\alpha_{ltm}$ is a proportionality constant, without using age or gender of the patient.

11. Apparatus according to claim 10, wherein the measuring unit for measuring the lean tissue mass comprises a bioimpedance measuring unit.

12. Apparatus according to claim 10, wherein the central processing unit is configured to determine a criterion for the prescription of a diuretic based on the determined glomerular filtration rate or creatinine clearance of the patient.

13. Apparatus according to claim 10, wherein the central processing unit is configured to determine a criterion for applying a renal replacement therapy to the patient based on the determined glomerular filtration rate or creatinine clearance of the patient.

14. Apparatus according to claim 10, adapted for a patient undergoing a renal replacement therapy, wherein the first receiver is configured to receive a first serum creatinine concentration at a first time between treatment sessions and to receive a second serum creatinine concentration at a second time between treatment sessions and wherein the central processing unit is configured to determine the patient's glomerular filtration rate or creatinine clearance based on the first creatinine concentration and on the second creatinine concentration.

15. Apparatus according to claim 14, including a third determination unit for measurement of the weight gain of the patient between the first time and the second time and wherein the central processing unit is configured to determine the patient's glomerular filtration rate or creatinine clearance based on the weight gain of the patient.

16. Apparatus according to claim 14, including a bioimpedance measurement unit for measuring the total body water by applying a bioimpedance measurement of a patient and wherein the central processing unit is configured to determine the patient's glomerular filtration rate or creatinine clearance based on the total body water of the patient.

17. Apparatus according to claim 14, wherein each of a first and a second mode of operation is defined for the central processing unit and wherein the central processing unit is configured to determine the glomerular filtration rate $Q_{gfr}$ by applying the formula:

$$Q_{gfr} = \frac{\alpha_{ltm} \cdot M_{LT_m}}{\beta_{ts} \cdot [Cr]_s},$$

wherein $M_{LTm}$ is the lean tissue mass of the patient, $[Cr]_s$ is the serum creatinine concentration, and $\alpha_{ltm}$ and $\beta_{ts}$ are proportionality constants in the first mode of operation and wherein the central processing unit is configured to operate wherein the patient is undergoing intermittently a renal replacement therapy, and wherein the first receiver is configured to receive a first serum creatinine concentration at a first time between treatment sessions and to receive a second serum creatinine concentration at a second time between treatment sessions and wherein the central processing unit is configured to determine the patient's glomerular filtration rate or creatinine clearance based on the first creatinine concentration and on the second creatinine concentration in the second mode of operation.

18. Computer-readable non-transitory medium comprising instructions for the execution of a method according to claim 1 when the instructions are executed on a computer.

* * * * *